United States Patent [19]

Jackson et al.

[11] 4,160,386

[45] Jul. 10, 1979

[54] ULTRASONIC INSPECTION SYSTEM INCLUDING APPARATUS AND METHOD FOR TRACKING AND RECORDING THE LOCATION OF AN INSPECTION PROBE

[75] Inventors: Jerry L. Jackson; Theodore L. Allen, Jr.; Wayne T. Flach; William D. Jolly; Steve A. Cerwin, all of San Antonio, Tex.

[73] Assignee: Southwest Research Institute, San Antonio, Tex.

[21] Appl. No.: 804,931

[22] Filed: Jun. 9, 1977

[51] Int. Cl.$^2$ ............................................. G01N 29/04
[52] U.S. Cl. .................................... 73/625; 73/622; 73/633
[58] Field of Search ............... 73/67.6 R, 67.7, 67.8 S, 73/71.5 US, 620, 640, 641, 618, 622, 633; 250/203 R

[56] References Cited

U.S. PATENT DOCUMENTS

| | | | |
|---|---|---|---|
| 2,520,297 | 8/1950 | Anderson | 73/67.5 R X |
| 3,715,914 | 2/1973 | Gross et al. | 73/67.7 |
| 3,988,922 | 11/1976 | Clark et al. | 73/67.8 SX |

*Primary Examiner*—C. A. Ruehl
*Attorney, Agent, or Firm*—Hubbard, Thurman, Turner, Tucker & Glaser

[57] ABSTRACT

An ultrasonic inspection system for inspecting objects, such as pipe, is disclosed which includes an ultrasonic inspection probe or search unit, and the usual ultrasonic transducers and electronics associated with the probe. The system also includes novel apparatus for continuously tracking and recording operation with respect to a reference point or area, on the object being inspected. For this purpose, the inspection probe includes one or more sources of radiant energy which are periodically actuated as the probe is moved about the object being inspected, and a plurality of receiving devices or microphones located at a fixed relationship with respect to the area being inspected or to a known reference point on the area, such as a weld. The location of the probe can be determined and recorded from information obtained by receipt of the signals from the source of radiant energy by two or more of the receiving devices. In order to permit the yaw of the inspection probe with respect to the centerline of the pipe to also be determined, and more accurately locate the inspection transducer of the probe at least two sources of radiant energy may be utilized at the inspection probe and the respective sources may be actuated at different time intervals to avoid interference between the tracking signals from the respective sources.

41 Claims, 9 Drawing Figures

ULTRASONIC INSPECTION SYSTEM INCLUDING APPARATUS AND METHOD FOR TRACKING AND RECORDING THE LOCATION OF AN INSPECTION PROBE

This invention relates to ultransonic inspection techniques for metal objects such as pipe, and in one of its aspects to an ultransonic inspection system including novel apparatus and methods for tracking and recording the location of an inspection probe relative to a fixed reference point or area on the object being inspected. In another aspect of this invention it relates to such apparatus and methods for use with a manual inspection probe being used to inspect, for example, the area immediately adjacent the transverse or butt weld joining two pipes to form a pipeline.

Pipe for use in pipelines for transporting volatile or contaminable fluids, or other substances that are potentially dangerous or harmful to the environment around the pipeline, is generally meticulously inspected prior to installation and actual useage. This inspection (which may be made by use of ultrasonics) includes inspection of the wall of the pipe, the longitudinal or seam weld along the length of the pipe, and the transverse or butt welds joining adjacent pipes together to form the pipe line. While these inspections are necessarily expensive and time consuming, they are necessary to meet various industrial codes and governmental requirements relating to the production and installation of such pipeline. During installation of the pipeline, it is, in many cases, either buried in the ground or wrapped with insulation making subsequent and periodic inspection of the whole pipeline difficult. In many installations, however, periodic inspections are required of the butt welds connecting the pipes together to form the pipeline, and of the area immediately adjacent the butt welds where defects are most likely to occur because of the stresses placed on that area of the pipe during welding and handling operations. An example where such periodic inspections are required is on pipelines used in nuclear powered electrical generating stations and other installations using nuclear reactors, where substances that are dangerous to the surrounding environment are likely to be handled and transported.

The butt weld itself is circular, substantially uniform, and fixed in location. For this reason, various techniques have been provided by the prior art to automatically inspect the butt weld and provide tracking and the recording of information concerning the location of the inspection probe and the condition of the weld at any point along it and at any time during the inspection. However, the most accurate way to inspect the area immediately adjacent the butt weld (i.e., about six inches on either side of the weld) is to use a manual inspection probe and to inspect this area manually under the control of a skilled operator. This is because the use of automatic inspection techniques to inspect this area is generally complicated by the fact that it is usually necessary to peel back insulation or dig around the area to be inspected, so that the use of relatively bulky inspection equipment utilizing motors and gears necessary for automatic operation is difficult. Furthermore, automatic inspection techniques have not proven to be as effective as manual inspection with a skilled operator who can slowly scan and examine the area of potential defects with special care which is more difficult to accomplish with an automatic inspection probe.

One of the difficult problems in using a manual inspection probe, which generally follows no preset path of movement, is providing tracking information concerning the location of the probe with respect to a fixed reference point, such as the butt weld, at any given moment during the inspection operation. This information is necessary in order to be able to correlate the information received concerning the condition of the pipe with the actual location of the condition on the pipe. It is possible for the operator to continuously observe a read-out device (such as a chart or scope) indicating the condition of the pipe as it is being inspected and to manually stop the operation and mark the location of the probe on the pipe when a problem area is indicated. However, it is much more desirable for the operator to be able to make his inspection scan without interruption and to have tracking information, which is correlated with the information concerning the condition of pipe, automatically recorded for future study and reference. While a number of prior art patents disclose systems for indexing and positioning an ultrasonic probe on a workpiece at a desired location or along a desired path, none of these references disclose methods and apparatus for determining the location of a probe that is randomly moved about a workpiece to provide for automatic and continuous recording of information relative to that location. Examples of such patents are U.S. Pat. Nos.:

3,857,052; 3,894,425; 3,233,450; 3,914,986; 3,898,838; 3,924,452; 3,135,109; 3,005,335; 2,989,865; 3,086,390; 3,690,311; 3,233,449; 3,960,006; 3,762,496; 3,895,685; 3,678,736; 3,721,118; 3,969,926; 3,981,184; 3,985,022; 3,985,024.

Thus, the primary object of this invention is to provide apparatus and methods for providing for tracking and recording of the relative location of an inspection probe with respect to a fixed reference point on an object being inspected, so that the manual inspection operation can be carried out without the necessity of the operator continually marking and correlating inspection and tracking information during the operation.

Another object of this invention is to provide such apparatus and methods which can also provide information concerning the yaw or angular orientation of the inspection probe.

Another object of this invention is to provide such apparatus and methods for use in an automatic data processing system for storing and reading out and correlating the location of the inspection probe at any point in time with the condition of the object being inspected at that location.

Since the inspection after installation of the butt weld and area adjacent it must take place in the field, and the space provided about the pipe may in some cases be limited, a further object of this invention is to provide for apparatus and methods which satisfy the above objects while also providing for portable operation, operation in remote and inaccessible areas, and operation in relatively confined spaces.

These and other objects of this invention, which will be apparent upon consideration of the appended claims and drawings, and of the detailed description of this invention, are accomplished by providing at least one source of radiant energy, on or in fixed relationship with the inspection probe, and at least two separate receiving devices which are located at some fixed and known location with respect to the area being inspected, or at a fixed and known distance from a known reference point on the object being inspected, such as a weld. In this manner the source of radiant energy can be periodically activated during inspection, for example, at a fixed repetition rate during inspection, and the distance from the source to each of the receiving devices measured to determine the location of the source by triangulation.

The data concerning this location of the probe, as well as the ultrasonic data, can be continuously recorded in the field and at a later date fed into a digital computer for processing and correlating to provide a permanent and useful record of the inspection.

In the preferred embodiment of this invention illustrated herein, airborne sound waves are generated by two spark gap transmitters located on or near opposite sides of the inspection probe to provide the radiant energy tracking signals. The receiving means includes an array of two or more (six are used in the preferred embodiment illustrated) microphones mounted on the object being inspected at a fixed and known distance from a reference point on the object (such as the butt weld referred to, or the location of the microphones themselves can be the reference point). The spark gaps are alternately and periodically pulsed and resultant signals picked up by each of the microphones. Means is also provided for detecting the relative times of arrival of the tracking signals at each of the microphones after they are generated, and the time of arrival of the two first signals is determined, as well as the identification of which pair of microphones received the first two signals. This information is then read out on a display device and also stored either on a mechanical recording device or in a digital computer. The time of arrival of the information received can be utilized to determine the distance by triangulation from the active microphones and the spark gap generating the tracking signals, and thus the distance from the spark gap to the weld or other reference point. This information, which is continuously obtained and stored during the inspection operation, can also be automatically correlated with ultrasonic data obtained at the same time.

An alternative embodiment for generating and receiving the tracking signals is also illustrated in which optical tracking signals are utilized. Of course, it is contemplated that other types of radiant energy signals may also be employed with the present invention.

The form of signal generating, signal processing, signal displaying, and signal recording apparatus used with this invention may take many different forms. This is also true with respect to the ultrasonic subsystem utilized with the present invention.

This disclosure includes, for purpose of illustration of the preferred form of this invention, a complete ultrasonic inspection system including the ultrasonic data subsystem, the tracking data subsystem, and the signal display, storage and processing subsystem. This disclosure is not, however, intended to be limiting to the specific system or apparatus disclosed.

DETAILED DESCRIPTION OF THE DRAWINGS

In the drawings, wherein like reference numerals are used throughout to designate like parts, and wherein preferred embodiments of the present invention are illustrated;

Figure 1:
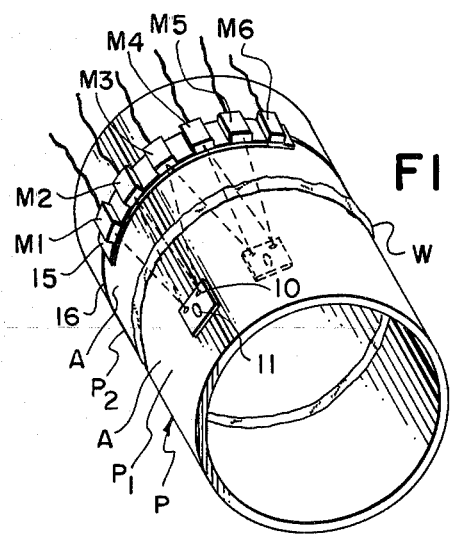
FIG. 1 is a perspective view in elevation illustrating two sections of pipe joined by a butt weld and wherein the apparatus of this invention is mounted on the pipe.

Referring now to FIG. 1, a pipeline P is illustrated as including two pipes P1 and P2 joined together at their ends by a butt weld W. The present invention is provided for inspection of the area A on each side of the butt weld W which may be, for example, six inches on either side of weld W. In order to provide for inspection of this area a hand-held inspection probe 10 which includes an ultrasonic trasmitting transducer 11 is provided. As is well known in the art, inspection probe 10 may include separate transmitting and receiving transducers so that ultrasonic waves are emitted from the transmitting transducer and echoes are received from flaws or other discontinuities by the receiving transducer, or a single transducer as illustrated may be provided for both the transmitting and receiving functions. As is also well known in the art, transducer 11 is connected to the necessary electronics for causing generation of the required ultrasonic waves and detection of echo signals, such as illustrated in more detail in FIG. 4. Details of the ultrasonic inspection transducer and its instrumentation form no part of the present invention and, of course, may take many forms.

Figure 2:
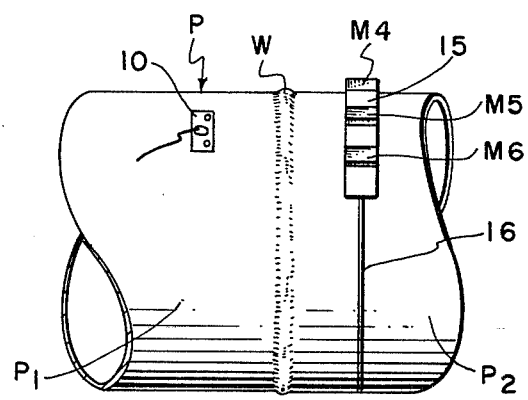
FIG. 2 is a side view of the apparatus of FIG. 1.
Figure 3:
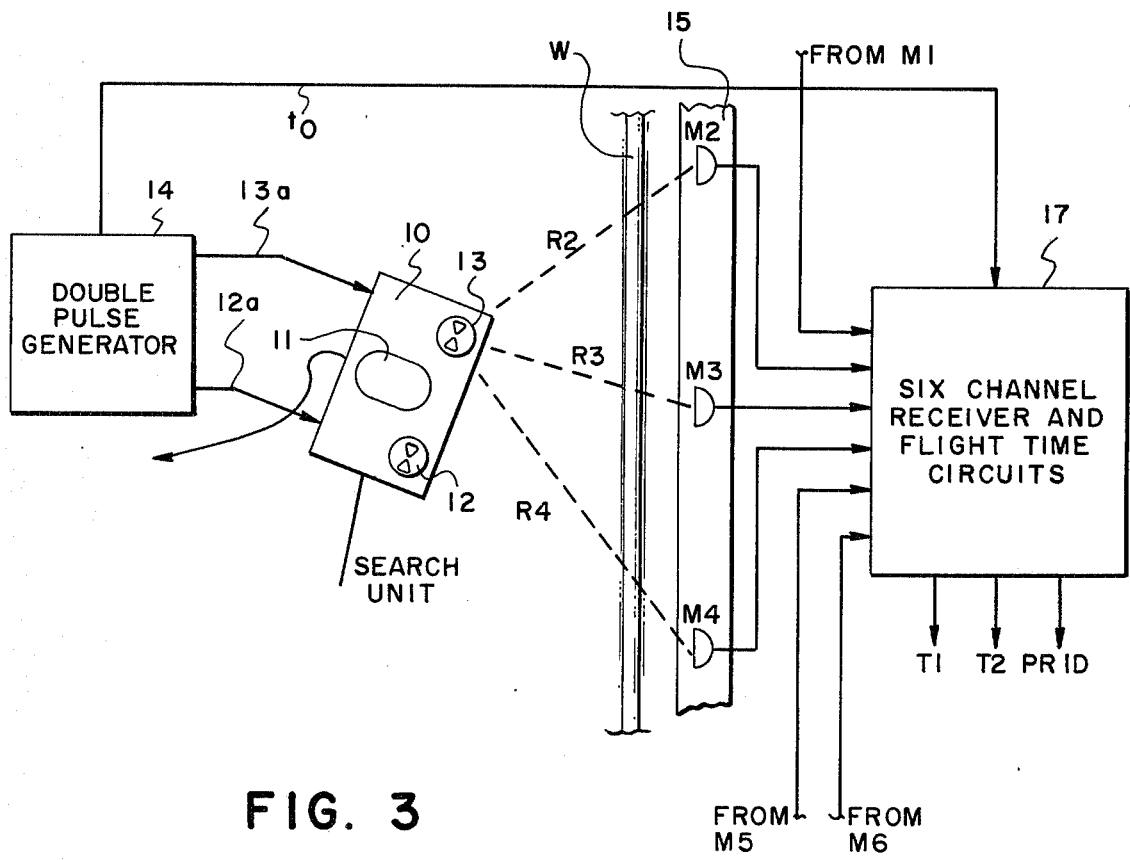
FIG. 3 is a schematic illustrating the arrangement of the components of the system of FIG. 1.

In order to provide information concerning the location of probe 10 during the scanning or inspection operation, at least one source of radiant energy is mounted on or in a fixed relationship with the probe to periodically produce tracking signals which may be detected and translated into information concerning the location of the probe with respect to weld W. As illustrated in FIGS. 1-3, it is preferred that two such sources 12 and 13, which may be spark gaps for generating air borne sound, be mounted on the opposite sides of probe 10 and be spaced an equal distance from transducer 11. Each of the spark gaps 12 and 13 may be actuated by pulses 12a and 13a received from a double pulse generator 14 to emit and transmit airborne sound waves in the vicinity of weld W which function as tracking signals. While the present invention is illustrated with the use of spark gaps to generate or launch the airborne waves, many other types of sources of radiant energy may be utilized for this purpose. For example, ultrasonic surface waves instead of airborne waves may be generated or, as illustrated with respect to FIGS. 7-9, optical signals may be generated and utilized for tracking signals in accordance with this invention. In actual practice it has been found that the use of airborne sound waves as the tracking signals is preferred over the use of surface waves because the airborne sound waves are less susceptible to interference from noise generated at the interface between the material being inspected and the receiving transducers used with the surface waves, as well as other forms of interference. However, surface waves may be useful for use in the present invention under certain conditions, but their use is less preferred.

The spark gaps 12 and 13 can be alternately fired in sequence at, for example, about two milliseconds apart, and a repetition rate of, for example, one pulse every 100 milliseconds for each spark gap. When each spark gap fires it creates a sharply rising airborne wave which can be detected by a microphone or similar means.

In addition to the sources of radiant energy described, this invention further requires receiving means for detecting the tracking signals from the radiant energy sources and translating the information received from them into information proportional to, or directly indicating the distance between the transducer and a fixed point. For example, in the embodiment of this invention illustrated in FIGS. 1 and 2 butt weld W may be a fixed reference point, so that it is convenient to locate the transducer along the length of pipeline P at a distance with respect to the butt weld. Also, in order to further identify the location of the transducer about the circumference of the pipeline it is convenient to locate it with respect to a reference point along the length of the pipe, such as the longitudinal seam weld or the center line of the pipe. An important feature of the present invention is that the tracking signals and the information derived therefrom can be continuously provided and recorded during an inspection operation even though the probe movement is random.

As illustrated in FIG. 1 the means for receiving the tracking signals from spark gaps 12 and 13 includes a plurality of receivers or microphones M1 through M6 which are mounted on a belt or harness 15. Belt 15 includes a strap 16 for securing belt 15 about the pipeline as illustrated in FIG. 2. By way of example, the number and arrangement of microphones may be such that approximately ⅓ of the circumference of the pipeline is covered by belt 15 and the remainder of the circumference of the pipeline is encircled by strap 16. In the embodiment of this invention illustrated six microphones are utilized, however, it is to be understood that this number can be varied as long as a sufficient number of microphones are used so that they can be placed close enough together to insure that a tracking signal from either one of the spark gaps 12 or 13 will be received at all times by at least two of the microphones no matter where probe 10 is located in the area of interest A. On the other hand, the microphones should be spaced sufficiently far apart so that the time of arrival of any signal from spark gaps 12 and 13 is distinctive enough at each of the microphones to permit use of only two signals from the bank of microphones M1–M6 to determine the location of the respective spark gaps.

During use of the present invention belt 15 is mounted on pipeline P at a fixed and known distance from weld W. As illustrated in FIG. 3 when spark gap 13 is actuated, it will emit airborne tracking signals (a traveling wave front) which are the signals received respectively by each of the microphones M1–M6. The tracking signals are represented in FIG. 3 by the distance from R1 to R6. Each one of the microphones M1–M6 is connected to a six channel receiver 17 which is also connected to double pulse generator 14 to receive a sync signal $t_o$ from the generator each time one of the spark gaps 12 and 13 is pulsed. Receiver 17 also includes a plurality of flight time circuits which measure the time from the receipt of the sync signal $t_o$ to the arrival of the first two of the tracking signals received, and provides the outputs T1, T2 and PRID for each of spark gaps 12 and 13 as shown in FIG. 3. The T1 output of the flight time circuit is the flight time to the microphone nearest to the spark gap being located, and T2 is the flight time to the second nearest microphone. The pair identification signal (PRID) identifies the microphone pair that is closest to the spark gap being located and their order of closeness.

The flight times, T1 and T2, are used to compute the distance from the spark gap to the microphones. Using these distances, the position of the spark gap relative to the weld W can also be computed. The precision of this computation depends, in part, on the precision with which the microphones have been located relative to weld W.

Figure 4:
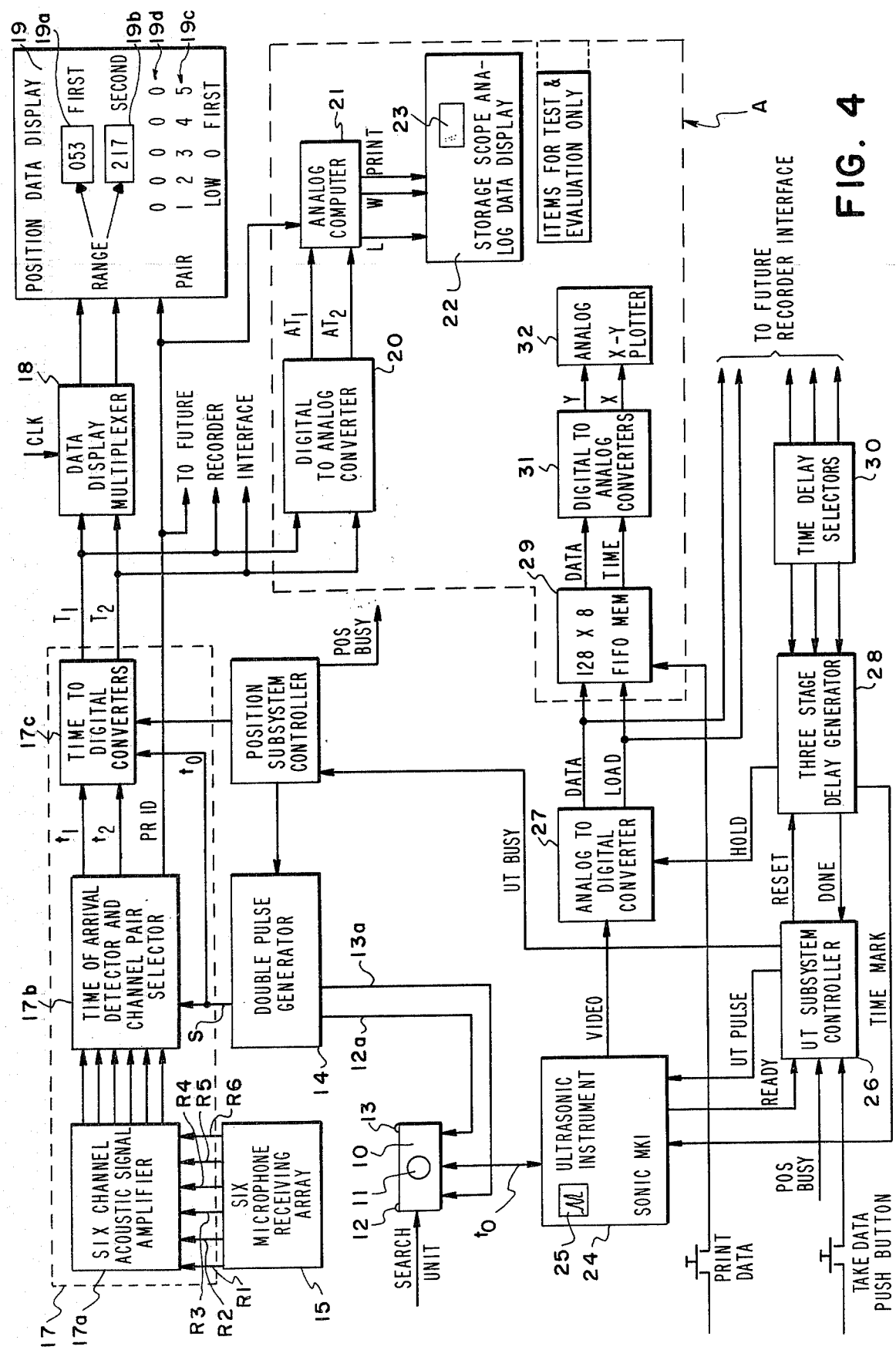
FIG. 4 is an overall block diagram of an ultrasonic inspection system utilizing the principals of this invention.

FIG. 4 illustrates the total system that was developed, fabricated, and tested to utilize the present invention in association with an ultrasonic system using a hand-held inspection probe. As illustrated in FIG. 4 receiver 17 includes a six channel acoustic signal amplifier 17a, and the flight time circuit includes a time of arrival detector 17b. Thus, the signals which have traveled the distance R1 to R6 are amplified and conducted to the time of arrival detector 17b which also includes a voltage comparator circuit, a channel pair selection circuit and a pair of time to digital converters 17c each of which includes a counting circuit.

The voltage comparator circuit marks the time of arrival at the instant the amplified signal voltage exceeds a set threshold voltage. As soon as two times of arrival are marked, all other channels are inhibited, the active pair of microphones is identified, and the order of signal arrival is also noted. These last two items of information constitute the PRID data (a 4-bit byte) that is passed to a display panel and to a computer as hereinbefore explained. The pulse signals t1 and t2 are the outputs of the time of arrival detector 17b that signal the arrival times of the first and second signals, respectively from microphones M1 to M6. The pulse $t_o$ is generated within double pulse generator 14, and its leading edge is closely coincident with the firing of a spark gap. The counters in the time-to-digital converters 17c start counting on receiving $t_o$. The first counter stops on receiving t1, and the second, on receiving t2. The counters are preferably 8-stage binary counters driven by a clock with a period of 3 microseconds. The output of these counters represents the flight time of the acoustic pulse from the spark gap to the two nearest microphones. The time representations are, consequently, 8-bit numbers in which the least significant bit corresponds to 3 microseconds. These binary time representations are indicated by output signals T1 and T2 from converters 17c as shown in FIG. 4.

Signals T1 and T2 are time multiplexed in a data display multiplexer 18 connected to the outputs of converters 17c and are displayed on a position data display panel 19 in 3-digit octal numbers using LED (light emitting diodes) type readouts 19a and 19b. Readout 19a displays the position information for the first received signal from microphones M1 to M3 and readout 19b the second received signal. In addition to the numeric display of T1 and T2, there are five LED indicators (1, 2, 3, 4, 5), generally represented by the reference numeral 19c, on position data display panel 19 that indicate which pair of microphones M1 to M6 were the first to receive the acoustic tracking signal. Another LED indicator (represented generally by the reference numeral 19d) indicates which member of the pair of microphones M1 to M6 received the first signal.

In order to permit on line evaluation of the positional information received, and computation of the position of the respective spark gap, an analog computer can be provided for use in the system of FIG. 4, or data can be recorded for later processing in an analog computer. Where the computer is connected on line as shown in FIG. 4, signals T1 and T2 can be converted to analog form by a digital to analog converter 20 and fed to such an analog computer 21. The signal PRID is also fed into the analog computer 21. Analog computer 21 uses these inputs to compute the coordinates of each spark gap 12 and 13 which may be referred to for purposes of identification as the "L" and "W" coordinates. "W" is defined as the perpendicular distance from the centerline of the weld W to the spark gap, in question, and "L" is defined as the distance along a line parallel to the centerline of the weldment from an established reference line to the spark gap. The generated voltages, representing magnitudes of W and L are impressed upon Y and X inputs of an oscilloscope or storage scope 22 connected to the output of analog computer 21.

When the computation of the desired coordinate information for either spark gap is complete, analog computer 21 sends a "print" command to storage scope 22 causing it to display a dot on its screen 23. The dot will remain on the screen until it is erased by pushing on erase button (not shown) on the front panel of the oscilloscope. Storage scope 23 is calibrated so that there is an established correspondence between the X-Y screen coordinates of screen 23 and the W-L weldment coordinates. As further position information is received by the system, the positions of both spark gaps are displayed on screen 23, and, as the search unit is moved, two loci of dots are drawn on the screen to indicate this movement. The skew angle or yaw of the search unit is readily apparent and can be reasonably well estimated from the relative positions of the dots on the screen.

In the event that the computer is not connected on line as described, signals T1, T2 and PRID can be interfaced with a magnetic recording device for storing the positional information for later processing and computation along with the ultrasonic information generated during the inspection operation.

The ultrasonic data subsystem of the embodiment of this invention shown in FIG. 4 consists basically of a conventional ultrasonic instrument 24 for acting on the echo signals S received from transducer 11 to provide a video display of the echo signals on a scope 25, and a means for converting the video signal it produces into a sequence of digital numbers. Ultrasonic instrument 24 may be modified from the conventional arrangement to provide for proper synchronization between the instrument and the digitizing circuitry and for buffering the received ultrasonic output. When the ultrasonic transmitter is ready to be pulsed, instrument 24 sends a READY signal to the ultrasonic digitizer controller circuit 26 which initializes all elements of the digitizing subsystem and returns a sync pulse signal to the ultrasonic instrument. On receiving the sync pulse, the ultrasonic instrument transmits an ultrasonic signal and subsequently detects the return echoes. The received ultrasonic signal derived from these echoes is passed on to an analog-to-digital (A-to-D) converter 27 connected to the output of ultrasonic instrument 24. At some selected time after transmitting the ultrasonic pulse, a HOLD signal is sent by a three-stage delay generator 28 to A-to-D converter 27. This signal causes A-to-D converter 27 to capture the amplitude of the received ultrasonic signal existing at that instant and to convert it into a digital number. When this conversion is complete, the digital number is sent as data to a FIFO (first in, first out) memory 29 and a LOAD signal is also sent to cause the FIFO memory to store the data.

This sequence of data gathering events follows each ultrasonic pulse. For purposes of explaining the specific embodiment of this invention shown in FIG. 4, a data gathering cycle is defined as a fixed number of ultrasonic pulses, each followed by a sequence of data gathering events. On the initial sequence of events, the HOLD signal follows the ultrasonic pulse by an interval of time established by the instrument operator through the time delay selectors 30 in delay generator 28. On each succeeding sequence, the interval of time between ultrasonic pulse and HOLD is automatically lengthened by a fixed increment. Therefore, for example, on the tenth sequence, the interval is nine increments longer than it was on the first sequence. The repetition of the sequence continues until a fixed number of sequences have been accomplished. This number is also established by the operator through the time delay selectors 30. In a model of the FIG. 4 embodiment actually built and tested, the time increment was chosen to be 0.4 microseconds so that, if the operator set the time delay selectors 30 to give a digitized span of 40 microseconds, this setting would establish the number of sequences at 100. Thus, for each data gathering cycle, the received ultrasonic signal is sampled in 100 places and 100 data words are loaded into the FIFO memory.

The 128×8 FIFO memory 29 accepts data from A-to-D converter 27 until it is full. The number of data gathering cycles that can be accomodated depends, of course, on the number of samples per cycle. During test and evaluation of the model of the FIG. 4 embodiment of this invention, two cycles were commonly accomodated. After the FIFO memory is full, it remains idle until it receives a print data command initiated by the operator through a panel switch (not shown). The print data command starts a data readout cycle during which the FIFO memory sends all of its data, in a sequence of 8-bit bytes, to a D-to-A converter 21. An 8-bit binary counter in memory 29 counts the data bytes as they are being sent, and the digital output of the counter is also sent to the D-to-A converters. One converter converts the data byte to an analog voltage. This appears as the Y output of the D-to-A converter. Another converter converts the output of the binary counter into an analog voltage. This appears as the X output. The X and Y outputs of the D-to-A converters are connected to the corresponding inputs of an X-Y plotter 32. Thus, the digital data stored in the FIFO memory are converted into an analog display. This display is a reconstruction of the received ultrasonic signal that is digitized and stored in the FIFO memory.

Figure 5:
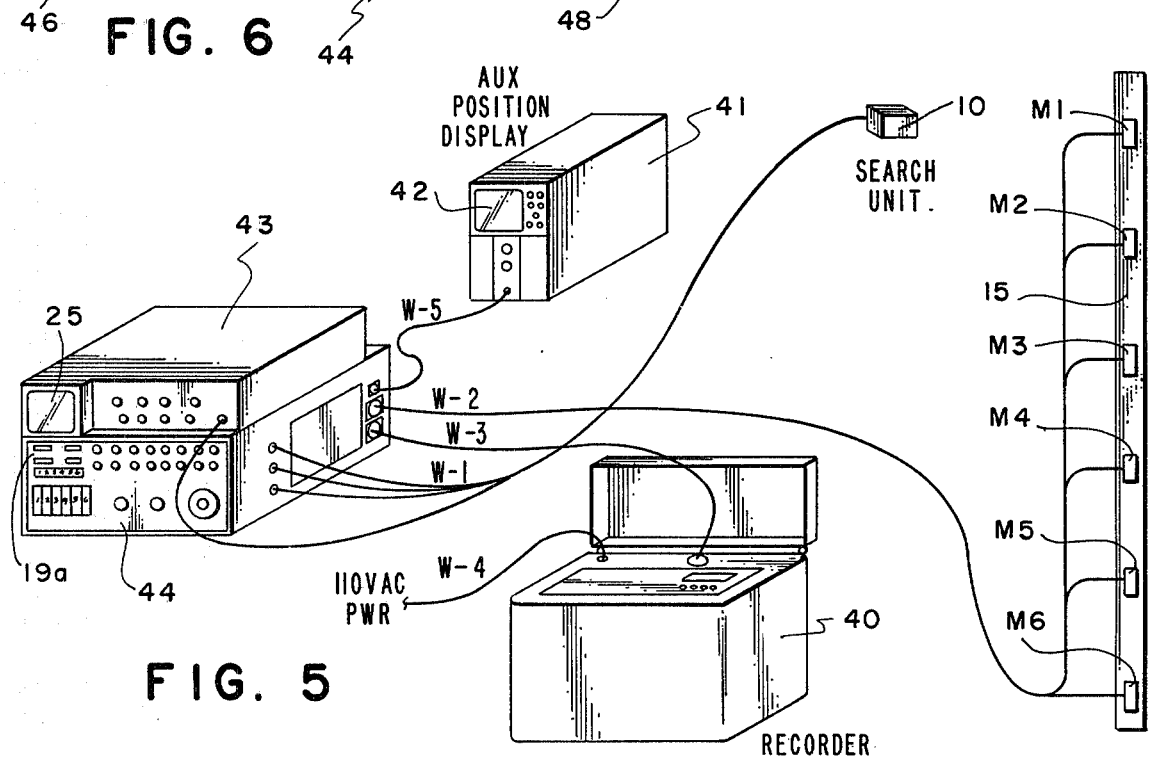
FIG. 5 is a perspective view of the various hardware components utilized with the present invention to provide for a complete inspection and recording operation at a remote location.

In field use of the ultrasonic system described, it may be desirable to provide for on line recording of the ultrasonic information for future read out and processing to avoid the necessity of bringing additional hardware to the field. In general those components inside the dotted line A in FIG. 4 need not be utilized in the field if some sort of permanent recording device is used to store the positional and ultrasonic data for future processing. FIG. 5 illustrates a typical system employing this invention for field use and includes a recorder 40 for recording the positional and ultrasonic data obtained for later processing, and an auxiliary position display device 41 for displaying on a scope 42 the positional data received during the inspection operation. The components of this system illustrated in FIG. 4 are otherwise contained in the unit 43 which displays the positional data on the read out devices 19a and 19b and the ultrasonic data on the scope 25.

Figure 6:
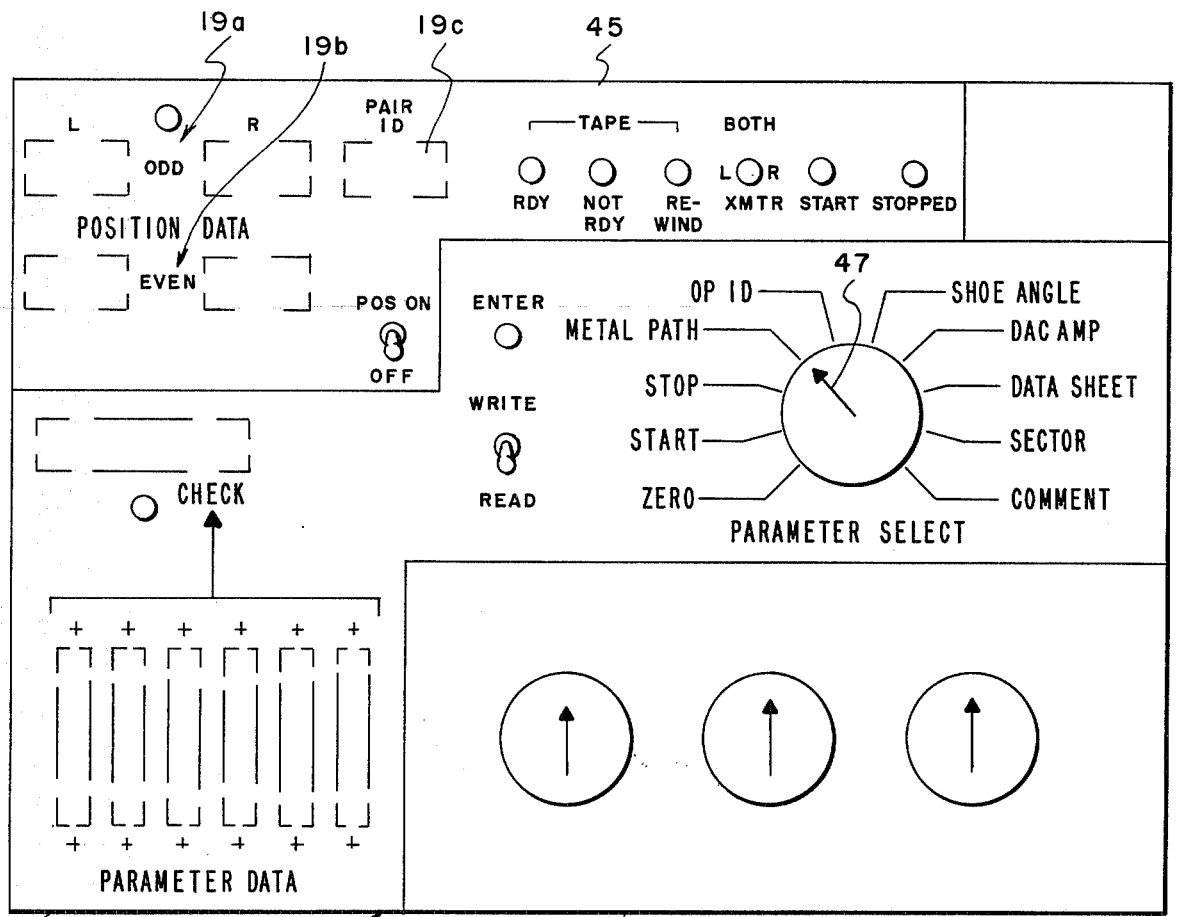
FIG. 6 is a view showing one arrangement of the front panel on the control apparatus employed with this invention.

FIG. 6 illustrates the preferred arrangement of the front panel 44 on unit 43 which can be utilized to control operation of the system of FIG. 4, along with display of positional data, while also providing for a permanent record of the various operating parameters involved in each inspection operation. In the blocked area 45 displays 19a and 19b can be provided along with pair identification display 19c. The position number for each of the two transducers (referred to as L and W in FIG. 6) can be displayed for the two microphones receiving the first two tracking signals.

The lower left-hand corner 46 of panel 44 provides for programming and read-out of parameter data that may be programmed onto the tape providing a permanent record of the inspection. A parameter select switch 47 is provided in order to permit the various parameters of inspection, including an operator identification code to be manually selected and stored. Thumb wheel switches 47a or similar devices may be used for actual programming of the parameter data. The boxed in portion 48 in the lower right corner of panel 44 may include a plurality of switches or control knobs for controlling the ultrasonic inspection conditions.

Figure 7:
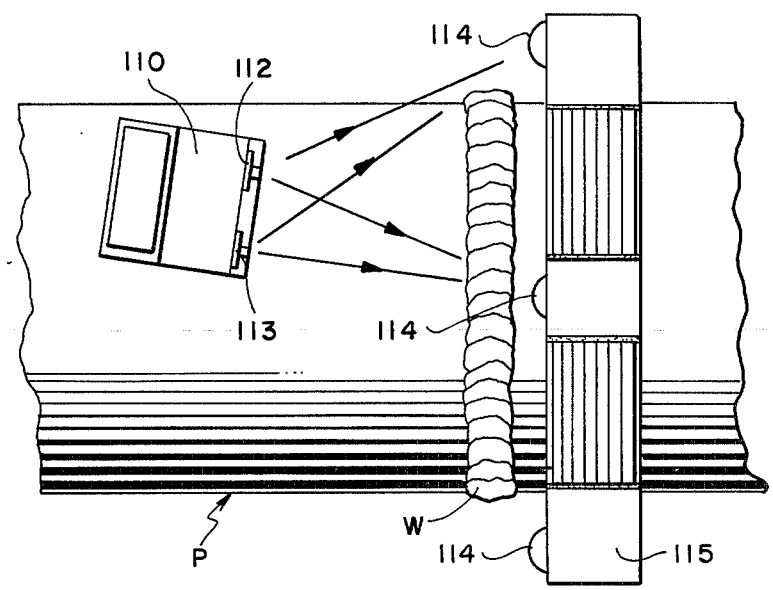
FIG. 7 is a schematic view of another embodiment of this invention for providing tracking and recording information of the location of the inspection probe.

Referring now to FIG. 7, another embodiment of this invention is illustrated in which optical signals are employed as the tracking signals. For this purpose, at least one omni-directional, infrared, light emitting diode (LED) is fixed to an ultrasonic inspection probe 110. It is preferred that two such diodes 112 and 113 be employed in order to determine the yaw or angle of inclination of the inspection probe. Also, a plurality of optical angular measurement devices 114 are placed around the pipe on a support member 15, the exact number of the devices 114 employed being dependent upon the size of the pipe and the height of LED's 112 and 113 above the pipe surface. Each of the devices 114 is capable of measuring the angle of incidence of light emitted from each of the LED's 112 and 113. Thus, the outputs of the two adjacent detection devices 114 can be combined and used to triangulate the position of the LED emitting the light, and thus the position of the transducer in probe 110.

Several methods may be employed to distinguish which LED is being detected when a two-LED system is used. These methods include: (1) the use of LED's with different optical wave lengths and the use of appropriate filters on the receivers; (2) modulating the LED's at two different frequencies with the signals being separated by the appropriate electronically tuned receivers; and (3) the preferred method of time multiplexing the LED's so that one LED is on when the other if off. This third method has the particular advantage that the same optical receiver and electronic amplifier may be used for both LED's, with the signals being separated by appropriate timing in the electronic processing unit.

Figure 8:
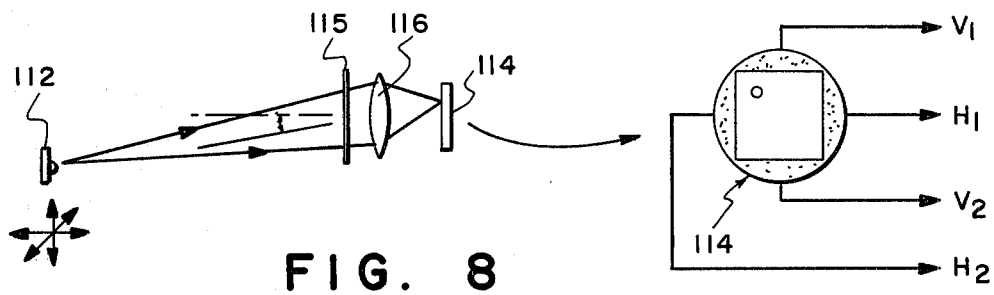
FIG. 8 is a schematic of the apparatus of FIG. 7.

The optical system used with the apparatus of FIG. 7 is illustrated schematically in FIG. 8 as including an infrared light emitting diode 112 such as a Texas Instruments TIXL 16A, which can emit approximately 50 mW of radiant energy at 950 nm over a $2\pi$ steradian field of coverage. An infrared bandpass filter 115 is provided ahead of a lens 116 to block visible room light. A short focal length 8 mm projector lens 116 (for example, 19 mm FL, f/1.6) is provided to image the LED onto the position sensitive detector 114. Each detector 114 is preferably a two-axis unit manufactured by United Detector Technology (PART No. SC-10), and provides vertical and horizontal voltages V1, V2, H1 and H2 which can be processed to yield the vertical and horizontal components of the incident beam angle received from LED 112 and 113.

Figure 9:
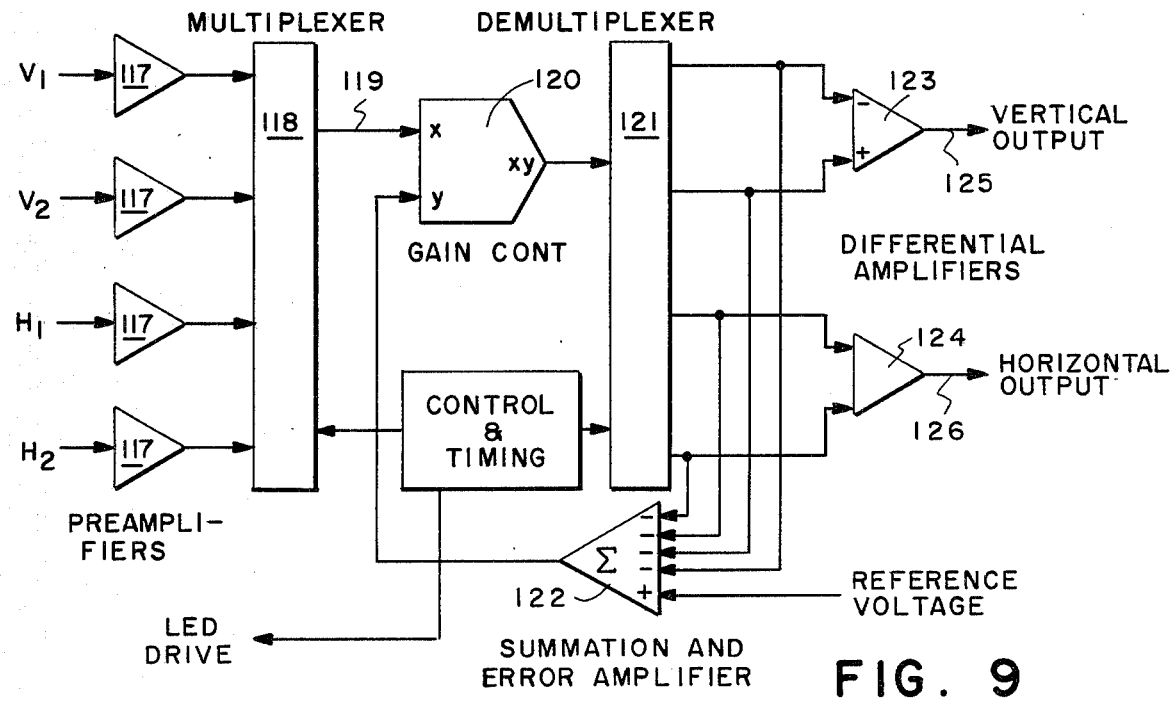
FIG. 9 is a schematic of the electronics employed with the apparatus of FIG. 7 in order to provide the desired tracking and recording information.

One embodiment of apparatus for processing the output of the detector is illustrated in FIG. 9. The primary requirement for the signal processing electronics is the removal of the influence of the amplitude of the impinging optical beam from the position measurement. Because the outputs of a position sensitive detector include both amplitude and position information, the amplitude component must be removed or normalized for the position measurement to be valid. This was accomplished by employing a high accuracy automatic gain control which electronically requires the sum of all outputs of the position detector to be constant. With the sum held constant, the two vertical signals V1 and V2 and two horizontal signals H1 and H2 are differenced to yield the position voltage. It has been found however, that linearity of the output is greatly improved by performing the summing and automatic gain control operations independently on the vertical and horizontal outputs. Several other electronic processing techniques would work equally well, including those which perform an analog division to remove the amplitude component from the position data. These schemes typically divide the difference by the sum, effectively normalized the amplitude component.

In operation of the optical tracking system of FIG. 7, each of the LED's 112 and 113 are preferably modulated at audio frequencies (for example, about 200 Hz) to allow the use of AC coupled, actively tuned preamplifiers for the detector outputs. This technique reduces the effects of ambient lighting conditions and also provides the possibility of filtering to produce an extremely clean signal with an excellent signal-to-noise ratio ($>50$ dB) and high stability. The 200 Hz carrier frequency was chosen as a convenient frequency well removed from any multiple of 60 Hz; however, any convenient frequency up to several tens of kilohertz can be used.

Each of the outputs, V1, V2, H1 and H2, of each detector 114 is conducted to one of the four preamplifiers 117 which are connected at their outputs to a multiplexer 118. The four preamplified signals are time multiplexed onto a common line 119 and fed to the X input of a four-quadrant analog multiplier 120. The output of multiplier 120, containing the gain conditioned signals, is fed into a demultiplexer 121 which detects and separates the four signals. The outputs of demultiplexer 121 provide four DC levels which are summed and compared to a fixed reference voltage in a summation and error amplifier 122, and the error voltage generated is fed back to the Y input of the analog multiplier, thereby effecting the closed loop AGC. This method of simultaneously gain controlling a number of different signals (i.e., multiplex, gain control, demultiplex) has the particular advantage that the gain control element (in this case an analog multiplier) conditions each signal in exactly the same manner, without regard to the transfer characteristics of the gain controlling element.

With the sum constant, the two horizontal and two vertical DC signals are differenced in amplifiers 123 and 124 to obtain the corresponding vertical and horizontal output voltages 125 and 126. Active low-pass filters (not shown) may be connected to the outputs of amplifiers 123 and 124 to reduce high frequency noise. By use of the imaging lens 116 ahead of detector 114, the outputs from amplifiers 123 and 124 will be a function of the angle of incidence of the beams of light from sources 112 and 113, and this information, after analog processing, can provide the position information for each LED 112 or 113, and this information can be digitized for final processing in a computer.

Several variations of the above described method exist. For example, the detection heads may be made sensitive to either planar angles or compound angles. If the area to be inspected is precisely defined and consists of a regular cylindrical surface, such as pipe, a planar angular detector would be sufficient to unambiguously define the transducer position. A more generally used (and more complex) solid angle device would be required for use on irregular or undefined surfaces.

The number of detectors 114 required to instrument a typical installation can also be varied. It is possible that as few as four detectors, equally spaced around the pipe, would be sufficient, with eight detectors being an example of the number of detectors that would be used although more or less could be used. Factors affecting the number of detectors required include the maximum field of coverage required of each detector (a function of the minimum source-to-detector distance), the diameter of the pipe, and the height of the LED above the pipe's surface.

There are also several practical methods of mounting the detectors 114 to the pipe. One method is to construct a strap-on belt with replaceable links. This chain-like structure could accommodate various size pipes by simply interchanging links with different lengths which have been pre-cut for different standard size pipe diameters. The detectors would be mounted on short link sections so that they may be used with any of the spacer links. This method would have the advantage that the spacing of the detectors around the pipes would be a function only of the pre-cut links, and, therefore, could be made quite accurate and repeatable with a minimum of operator alignment.

While it is preferred that the source (or sources) of radiant energy be located in the inspection probe as illustrated in FIGS. 3 and 7, two or more receiving devices can be mounted on the probe and a source (or sources) of radiant energy can be located on the pipe at a fixed distance from the weld or other reference point. This arrangement, however, is less preferred although it has worked successfully in connection with experiments by Applicants using surface waves for the radiated energy tracking signals.

As should be apparent from the foregoing, the present invention provides for the generation of accurate positional information identifying the location of an inspection probe at any time during inspection for processing and recording, and for in field use during inspection. The information obtained may also be provided for subsequent use in a data processing system analyzing the ultrasonic inspection data.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. In an ultrasonic inspection system for randomly inspecting along the surface of an object, said system including an inspection probe having at least one ultrasonic transducer, means for periodically pulsing the transducer to cause it to emit ultrasonic waves, and ultrasonic signal receiving and processing means including means for receiving echo signals from said object being inspected and for acting on the received echo signals to provide useful information concerning the condition of said object in the area being inspected, the improvement comprising, apparatus for providing tracking information relating to the location of the inspection probe at different and random locations on said object, and with respect to a fixed reference on said object, said apparatus comprising at least one source of radiant energy located at a known distance from one of said transducer or fixed reference, to provide a plurality of airborne sound tracking signals during the inspection operation; at least two signal receiving devices located at a known distance from one of said fixed reference or said at least one ultrasonic transducer, and located with respect to each other so that the distance from the source of radiant energy to each of said receiving devices can be detected and utilized to determine the location of said source of radiant energy with respect to the receiving devices; and means connected to receive the output signals from said receiving devices for responding to tracking signals received to detect the flight time of the airborne sound signals from said radiant energy source to each of the receiving devices and provide output signals indicative of the distances detected and also indicative of the orientation of the ultrasonic transducer with respect to the object being inspected.

2. The system of claim 1 wherein said source of radiant energy includes two such sources mounted on opposite sides of said inspection probe so that the angular orientation of said inspection probe can be determined.

3. The system of claim 2 wherein each of said sources of radiant energy is a spark gap transmitter for generating airborne sound signals.

4. The apparatus of claim 1 wherein each of said signal receiving devices is a microphone and further including means for mounting a plurality of said microphones on said object to be inspected at said known distance.

5. The system of claim 4 wherein said object to be inspected is a pipeline and said fixed reference on said object is a butt weld on said pipeline, and said microphone mounting means is a belt adapted to encircle the pipeline and said microphones are mounted on said belt with each microphone spaced equally apart from the adjacent microphone.

6. The system of claim 1 wherein said last mentioned means includes means for detecting which two of said receiving devices are the closest to said source of radiant energy and for providing an output signal representing the pair of receiving devices so identified.

7. The system of claim 1 further including means responsive to said output signals to provide for storage and display of data representing the the relative position of said probe at a selected point in time during the inspection operation.

8. The system of claim 7 wherein means provided to connect each of said output signals to a digital number and means is provided for displaying the digital numbers.

9. A tracking and recording system for use as a subsystem of an inspection system, and providing information indicative of the relative location of an inspection probe with respect to a fixed reference on an object being inspected, comprising in combination:
at least one source of radiant energy adapted to be mounted in a known relationship with said inspection probe;
means for causing said source of radiant energy to provide a plurality of airborne sound tracking signals;
at least two signal receiving devices adapted to be mounted in a known relationship with a fixed reference on said object being inspected for receiving tracking signals from said source of radiant energy, said receiving devices being located with respect to each other so that the time of travel of the tracking signals to each of said receiving devices can be detected and utilized to determine the location of said source of radiant energy with respect to the receiving devices; and
means connected to receive the output signals from said receiving devices for detecting the flight time of the airborne sound signals from said radiant energy source to each of the receiving devices for determining the relative distance from the source of radiant energy to at least two of said receiving devices, and providing output signals indicative of the distances determined and also indicative of the orientation of the inspection probe to the object being inspected.

10. The system of claim 9 wherein said source of radiant energy includes two such sources mounted on opposite sides of said inspection probe so that the angular orientation of said inspection probe can be determined.

11. The system of claim 10 wherein each of said sources of radiant energy is a spark gap transmitter for generating airborne sound signals.

12. The apparatus of claim 9 wherein each of said signal receiving devices is a microphone and further including means for mounting a plurality of said microphones on said object to be inspected at a known distance from said fixed reference on said object.

13. The system of claim 12 wherein said object to be inspected is a pipeline and said fixed reference on said object is a butt weld on said pipeline, and said microphone mounting means is a belt adapted to encircle the pipeline and said microphones are mounted on said belt with each microphone spaced equally apart from the adjacent microphones.

14. The system of claim 9 wherein said last mentioned means includes means for detecting which two of said receiving devices are the closest to said source of radiant energy and for providing an output signal representing the pair of receiving devices so identified.

15. The system of claim 9 further including means responsive to said output signals to provide for storage and display of data representing the relative position of said probe at a selected point in time during the inspection operation.

16. The system of claim 15 wherein means is provided to connect each of said output signals to a digital number and means is provided for displaying the digital numbers.

17. A method of tracking and recording the location of a randomly positioned inspection probe in a system provided for inspection of an object, comprising the steps of:
simultaneously generating a plurality of airborne sound tracking signals from a source of radiant energy located at a fixed relationship with the probe being located;
detecting at least two of said tracking signals in at least two receiving means each having a known location relative to the object being inspected,
determining the distance from the source of radiant energy to each of the two receiving means,
and utilizing the distance information obtained to detect the flight time of the airborne sound signals from said radiant energy source and determine the location of said source of radiant energy from said receiving means, and the orientation of said inspection probe.

18. The method of claim 17 wherein said source of radiant energy includes two such sources mounted on opposite sides of said inspection probe so that the angular orientation of said inspection probe can be determined.

19. The method of claim 18 wherein each of said source of radiant energy is a spark gap transmitter for generating airborne sound signals.

20. The method of claim 17 wherein said object to be inspected is a pipeline and each of the receiving means is located at a known distance from a butt weld on said pipeline.

21. In an ultrasonic inspection system for randomly inspecting along the surface of an object, said system including an inspection probe having at least one ultrasonic transducer, means for periodically pulsing the transducer to cause it to emit ultrasonic waves, and ultrasonic signal receiving and processing means including means for receiving echo signals from said object being inspected and for acting on the received echo signals to provide useful information concerning the condition of said object in the area being inspected, the improvement comprising, apparatus for providing tracking information relating to the location of the inspection probe at different and random locations on said object, and with respect to a fixed reference on said object, said apparatus comprising at least one source of radiant energy located at a known distance from one of said transducer or fixed reference to provide a plurality of optical tracking signals during the inspection operation; at least two signal receiving devices located at a known distance from one of said fixed reference of said at least one ultrasonic transducer, and located with respect to each other so that the distance from the source of radiant energy to each of said receiving devices can be detected and utilized to determine the location of said source of radiant energy with respect to the receiving devices; and means connected to receive the output signals from said receiving devices for responding to tracking signals received to detect the angle of incidence of the generated optical signals and provide output signals indicative of the distances detected.

22. The system of claim 21 wherein each of said sources of radiant energy is a light emitting diode for generating optical signals.

23. The system of claim 22 wherein said receiving devices are light sensitive detectors mounted spaced apart on said object to be inspected.

24. The system of claim 21 wherein said last mentioned means includes automatic gain control for processing said output signals to remove the amplitude component from the optical signals received so that the resulting signals are representative of only the angle of incidence of said optical signals.

25. In an ultrasonic inspection system for randomly inspecting along the surface of an object, said system including an inspection probe having at least one ultrasonic transducer, means for periodically pulsing the transducer to cause it to emit ultrasonic waves, and ultrasonic signal receiving and processing means including means for receiving echo signals from said object being inspected and for acting on the received echo signals to provide useful information concerning the condition of said object in the area being inspected, the improvement comprising, apparatus for providing tracking information relating to the location of the inspection probe at different and random locations on said object, said apparatus comprising at least two sources of radiant energy each located at a known distance from one of said ultrasonic transducer or a fixed reference on said object being inspected, to provide a plurality of tracking signals during the inspection operation; at least two signal receiving devices located at a known distance from one of said fixed reference on the object being inspected or from said ultrasonic transducer, and located with respect to each other so that the distance from the sources of radiant energy to each of said receiving devices can be detected and utilized to determine the location of said sources of radiant energy with respect to the receiving devices; and means connected to receive the output signals fom said receiving devices for responding to tracking signals received to provide output signals indicative of the distances detected and of the angular orientation of said inspection probe.

26. The system of claim 25 wherein said sources of radiant energy signals generate airborne sound signals and said last mentioned means detects the flight time of the airborne sound signals from said radiant energy sources to each of the receiving devices.

27. The system of claim 25 wherein said sources of radiant energy signals generate optical signals and said last mentioned means detects the angle of incidence of the generated optical signals.

28. The system of claim 25 wherein each of said sources of radiant energy is a spark gap transmitter for generating airborne sound signals.

29. The system of claim 25 wherein each of said sources of radiant energy is a light emitting diode for generating optical signals.

30. The apparatus of claim 26 wherein each of said signal receiving devices is a microphone and further including means for mounting a plurality of said microphones on said object to be inspected at said known distance.

31. The system of claim 30 wherein said object to be inspected is a pipeline and said fixed reference on said object is a butt weld on said pipeline, and said microphone mounting means is a belt adapted to encircle the pipeline and said microphones are mounted on said belt with each microphone spaced equally apart from the adjacent microphone.

32. The system of claim 27 wherein said receiving devices are light sensitive detectors mounted spaced apart on said object to be inspected.

33. The system of claim 25 wherein said last mentioned means includes means for detecting which two of said receiving devices are the closest to at least one of said sources of radiant energy and for providing an output signal representing the pair of receiving devices so identified.

34. The system of claim 26 wherein said last mentioned means includes means for detecting which two of said receiving devices are the closest to at least one of said sources of radiant energy and for providing an output signal representing the pair of receiving devices so identified.

35. The system of claim 25 further including means responsive to said output signals to provide for storage and display of data representing the relative position of said probe at a selected point in time during the inspection operation.

36. The system of claim 35 wherein means provided to convert each of said output signals to a digital number and wherein display means is provided for displaying the digital numbers.

37. The system of claim 27 wherein said last mentioned means includes automatic gain control for processing said output signals to remove the amplitude component from the optical signals received so that the resulting signals are representative of only the angle of incidence of said optical signals.

38. A method of tracking and recording the location of a randomly position inspection probe in a system provided for inspection of an object, comprising the steps of:
simultaneously generating a plurality of optical tracking signals from a source of radiant energy located at a fixed relationship with the probe being located;
detecting at least two of said tracking signals in at least two receiving means each having a known location relative to the object being inspected,
detecting the angle of incidence of the generated optical signals to determine the distance from the source of radiant energy to each of the two receiving means,
and utilizing the distance information obtained to determine the location of said source of radiant energy from said receiving means.

39. The method of claim 38 wherein said source of radiant energy includes two such sources mounted on opposite sides of said inspection probe so that the angular orientation of said inspection probe can be determined.

40. The system of claim 39 wherein each of said sources of radiant energy is a light emitting diode for generating optical signals.

41. The method of claim 38 wherein said object to be inspected is a pipeline and each of the receiving means is located at a known distance from a butt weld on said pipeline.

* * * * *